United States Patent [19]

Dimeff

[11] 4,055,764
[45] Oct. 25, 1977

[54] OPTICALLY SELECTIVE, ACOUSTICALLY RESONANT GAS DETECTING TRANSDUCER

[75] Inventor: John Dimeff, San Jose, Calif.

[73] Assignee: The United States of America as represented by the United States National Aeronautics and Space Administration, Washington, D.C.

[21] Appl. No.: 643,043

[22] Filed: Dec. 22, 1975

[51] Int. Cl.$^2$ .............................................. G01J 1/00
[52] U.S. Cl. .................................. 250/336; 250/343; 250/351
[58] Field of Search ............... 250/343, 344, 349, 350, 250/336; 13/23; 356/97

[56] References Cited

U.S. PATENT DOCUMENTS

| | | | |
|---|---|---|---|
| 3,005,097 | 10/1961 | Hummel | 250/343 |
| 3,426,202 | 2/1969 | Gay et al. | 250/350 |
| 3,476,934 | 11/1969 | Luft | 250/344 |
| 3,659,452 | 5/1972 | Atwood | 250/343 |
| 3,727,050 | 4/1973 | Kerr | 250/343 |
| 3,787,694 | 1/1974 | Owen | 250/343 |
| 3,820,901 | 6/1974 | Kreuzer | 356/97 |

Primary Examiner—Alfred E. Smith
Assistant Examiner—B. C. Anderson
Attorney, Agent, or Firm—Darrell G. Brekke; John R. Manning

[57] ABSTRACT

A gas analyzer is disclosed which responds to the resonant absorption or emission spectrum of a specific gas by producing an acoustic resonance in a chamber containing a sample of that gas, and which measures the amount of that emission or absorption by measuring the stength of that acoustic resonance, e.g., the maximum periodic pressure, velocity or density achieved. In the preferred embodiment, a light beam is modulated periodically at the acoustical resonance frequency of a closed chamber which contains an optically dense sample of the gas of interest. The light beam is introduced into the chamber through a window transparent to the radiation in the spectral band of interest and located at a position in the chamber which can support a pressure maximum during acoustical resonance of the gas within the chamber. Periodic heating of the absorbing gas by the periodically modulated light beam incident on the gas then causes a cyclic expansion, movement, and pressure within the gas. The amplitude of the excursions increases until an amplitude is reached where the increased losses involving the amplified motions, compressions and thermal cycles are just sufficient to account the cyclic radiation energy received through the window. A differential pressure transducer is located within the acoustically resonant chamber and coupled thereto by pipes, ports or by immersion so that one of its ports is exposed to large pressure excursions of the acoustically resonant gas while the other port is exposed to significantly smaller or zero pressure excursions or to large excursions of opposing phase. Improved performance is obtained by designing the sensitive element of the pressure transducer so that it is mechanically resonant at a frquency identical to the acoustical resonance frequency of the gas containing chamber. A transducing system is inclined for converting the pressure variations of the resonant gas into electronic readout signals.

7 Claims, 4 Drawing Figures

OPTICALLY SELECTIVE, ACOUSTICALLY RESONANT GAS DETECTING TRANSDUCER

The invention described herein is made by an employee of the United States Government and may be manufactured and used by or for the Government for governmental purposes without the payment of any royalties thereon or therefor.

BACKGROUND OF THE INVENTION

1. Field of the Invention

The invention relates to gas analyzing systems which measure periodic pressure variations occuring within an acoustically resonant gas sample contained within a sample chamber.

2. Description of the Priot Art

U.S. Pat. No. 3,005,097 disclosed a method and apparatus for analyzing mixtures of gases contained within a chamber. A beam of light is transmitted through the gas sample therein. The gas sample is subjected to periodic density variations produced by a reciprocating piston which is coupled to the chamber containing the gas. Variations in density within the chamber cause a periodic change in the light flux absorbed therein and transmitted therethrough into a gas contained within a second chamber. Gas heating within the second chamber is measured by transducing the change in capacitance produced by the deflection of a membrane which is part of a variable capacitor. The pressure transducer disclosed in U.S. Pat. No. 3,005,097 does not respond to pressure fluctuations induced within the gas sample at a frequency corresponding to an acoustical resonance of that gas sample in its container which is identical in frequency to the mechanical resonance of the deflecting diaphragm of the pressure transducer.

U.S. Pat. No. 2,951,938 discloses a gas analyzing system similar to that disclosed in U.S. Pat. No. 3,005,097. A source of energy is directed through a gas sample which is contained in a chamber that is divided into two parts by the membrane of a pressure transducer of the variable capacitance type. A source of radiation which impinges on the sample chamber is optically chopped at a frequency which produces vibrations of the diaphragm contained within the chamber if energy is absorbed within one of the parts of the chamber which is irradiated by the source of radiation. U.S. Pat. No. 2,951,938 discloses the use of a small leak between the two parts of the chamber to relieve slowly varying pressure differences which arise from a temperature differential between the two parts of the chamber without dissipating rapid pressure changes which cause the diaphragm to vibrate. However, the pressure transducer disclosed in U.S. Pat. No. 2,951,938 differs substantially from the present invention in that it does not respond to pressure fluctuations amplified by the action of an acoustic resonance within a chamber and detected by means of the enhanced displacement of a diaphragm whose mechanical resonance frequency matches that acoustical resonance frequency.

SUMMARY OF THE INVENTION

The disadvantages and limitations of the prior art transducing apparatus used in spectroscopic systems are obviated by the present invention which provides a gas detecting transducer for measuring variations in pressure occurring within a gas contained in a sample chamber which has improved sensitivity and improved immunity from environmental noise and drift.

In its broadest sense, the present invention comprises an apparatus selectively responsive to minute acoustical disturbance at a particular frequency. A first chamber is provided which contains a sample of the gas to be measured, the first chamber being designed to promote acoustical resonance of the gas therein contained at a selected frequency. A second chamber is provided which is divided into two parts by a pressure transducing diaphragm having a resonant response selectively sensitive to the frequency of the acoustical resonance, the second chamber being coupled to said first chamber by first and second conduits. The first conduit couples all pressure variations occurring within the first chamber including those at the acoustical resonance frequency and very low frequency fluctuations to the first part of the second chamber. The second conduit, is designed to couple only average or slowly varying pressure fluctuations caused by temperature fluctuations, etc. occurring within the first chamber to the second part of the second chamber. Correspondence between the mechanical resonance frequency of the diaphragm and the acoustic resonance frequency of the first chamber enhances the response characteristics of the pressure transducer at the resonance frequency and depresses response to pressure fluctuations at frequencies other than the resonance frequency. This selective response greatly enhances the transducing sensitivity of the pressure transducer in comparison to background noise introduced by random fluctuations of environmental temperature, vibration, etc. A transducing system is included for converting the pressure fluctuations occurring within the second chamber into electronic readout signals.

In a more limited sense, the present invention comprises a spectroscopic apparatus for measuring trace quantities of a selected gas occurring within a mixture of gases. When used with a spectroscopic apparatus, a sample chamber containing an unknown gas is mounted on the end of the first chamber to permit incident radiation to pass through the sample chamber and through the first chamber of the pressure transducing apparatus and out the other end thereof. The ends of the sample chamber and the first chamber of the pressure transducer are optically transparent to the wavelengths of energy which are incident upon the gas samples contained respectively in the sample chamber and in the first chamber of the pressure transducer. Inlet and exit gas ports are provided in the sample chamber for permitting the rapid changing of the gas sample contained within the chamber between tests procedures. A pressure varying apparatus is provided in the sample chamber to permit the production of periodic pressure fluctuations within the gas contained in the sample chamber. The side walls of the sample chamber and of the first chamber of the gas detecting transducer are highly reflective in the range of wavelengths in which the absorption characteristic of the gas contained in the first chamber is being examined.

DESCRIPTION OF THE PREFERRED EMBODIMENTS

Figure 1:
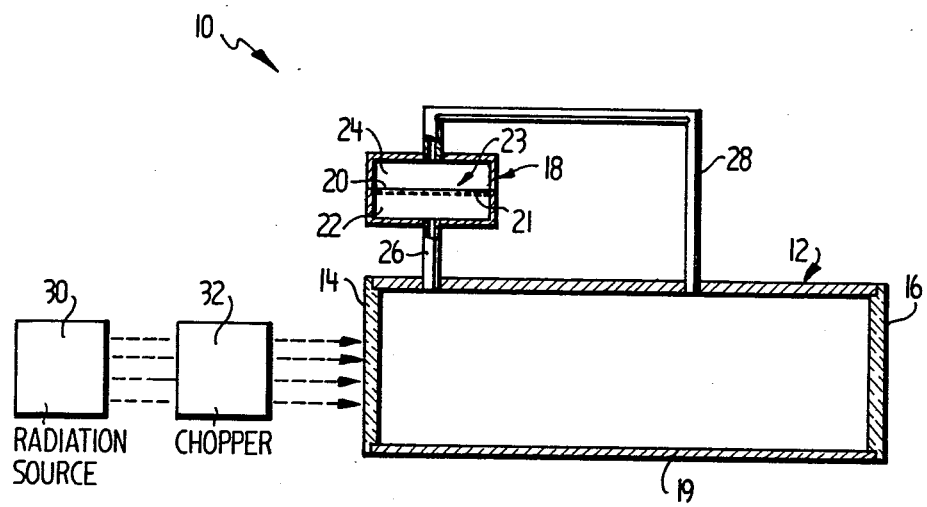
FIG. 1 is a schematic view of gas detecting transducer constructed according to the present invention.

Referring to FIG. 1, a gas detecting transducer 10 constructed according to the present invention may be described as follows. A first chamber 12 is provided which has a cylindrical shape that is closed by ends 14 and 16, to provide a configuration similar to an organ pipe and capable of supporting acoustical resonance of the gas contained therein in a longitudinal mode. Ends 14 and 16 are transparent to a spectrum of electromagnetic energy which includes the wavelengths which are absorbed by the gas or gases of interest. The side 19 of chamber 12 is highly relfective in the range of wavelengths being examined to enhance absorption of electromagnetic radiation by the gas or gases contained within the chamber 12. The optical thickness of the gas contained within chamber 12 is chosen to be less than half of the length of chamber 12 so that the gas contained within chamber 12 and nearest to window 14 may absorb a significantly larger portion of the incident radiation than is absorbed by the gas near window 16. A second chamber 18 has an electrically conductive pressure responsive diaphragm 20 disposed across the inside thereof to divide chamber 18 into two parts 22 and 24 respectively. An electrically conductive grid 21 is disposed adjacent to diaphragm 20 and electrically insulated therefrom. The diaphragm 20, grid 21 and the gas therebetween form a variable capacitor 23. The variable capacitor 23 is part of a transducing system which will be discussed below with reference to FIG. 3. First and second conduits 26 and 28 respectively couple the first chamber 12 to the first part of the second chamber 22 and the second part of the second chamber 24. The first conduit comprises a first means for coupling all pressure variations occurring within the first chamber including those at the acoustical resonance frequency of the first chamber as well as slowly fluctuating pressures to the diaphragm 20 disposed within the second chamber. The second conduit 28 comprises a second means for coupling only average and slowly varying pressure fluctuations occurring within the first chamber 12 to the side 24 of the diaphragm 20 disposed within the second chamber 18 and for simultaneously preventing transmission of pressure fluctuations at the acoustical resonance frequency of the first chamber 12 and the mechanical resonance frequency of the diaphragm 20. The pressure variations coupled by the second means to the second part of the second chamber are of the opposite phase as the pressure variations coupled by the first means to the first part of the second chamber. The function of the second conduit 28 is to relieve slowly varying pressure differences otherwise occurring between the first and second parts 22 and 24 respectively of the second chamber 18. The design of the first and second conduits is derived from well known acoustic equations. The first chamber 12, the second part 24 of second chamber 18 and conduit 28 comprise a double Helmholtz resonator. Radiation source 30 produces a beam of radiation which is transmitted through the optically transparent end sections 14 and 16 of chamber 12. A chopper 32 of well known construction periodically interrupts the radiation being emitted from source 30 at a frequency which is equal to the acoustical resonance frequency of chamber 12 and the mechanical resonance frequency of diaphragm 20. The radiation source 30 and chopper 32 comprise a means for inducing a standing wave within the gas contained in chamber 12. The standing wave is induced by periodic heating of the gas within chamber 12 and near window 14. Since chamber 12 is closed, organ-pipe-like structure, periodic heating causes a periodic increase in the pressure. Each successive increase is phased to reinforce the pressure initiated by the previous increase; the earlier increase having propagated to the end of chamber 12 near window 14 after having been reflected from window 16 in the period between the successive radiation pulses. The effect of this phased reinforcement of pressure near window 14 is to create a standing wave with a maximum pressure much greater than would result from a single heating cycle. Periodic pressure fluctuations occurring within chamber 12 as a result of the acoustic resonance therein are mechanically coupled to diaphragm 20. Because the mechanical resonance frequency of the diaphragm 20 is chosen to be equal to the acoustical resonance frequency of chamber 12, any periodic pressure fluctuations occurring within chamber 12 near the acoustical resonance frequency produce an unusally large mechanical deflection of diaphragm 20, substantially enhancing sensitivity of membrance 20 to acoustic pressure resonances occurring with chamber 12, while rejecting environmental noise occurring at other frequencies. The first and second chambers 12 and 18 may be filled with known concentrations of several different gases with dissimilar electromagnetic absorption spectra.

Figure 3:
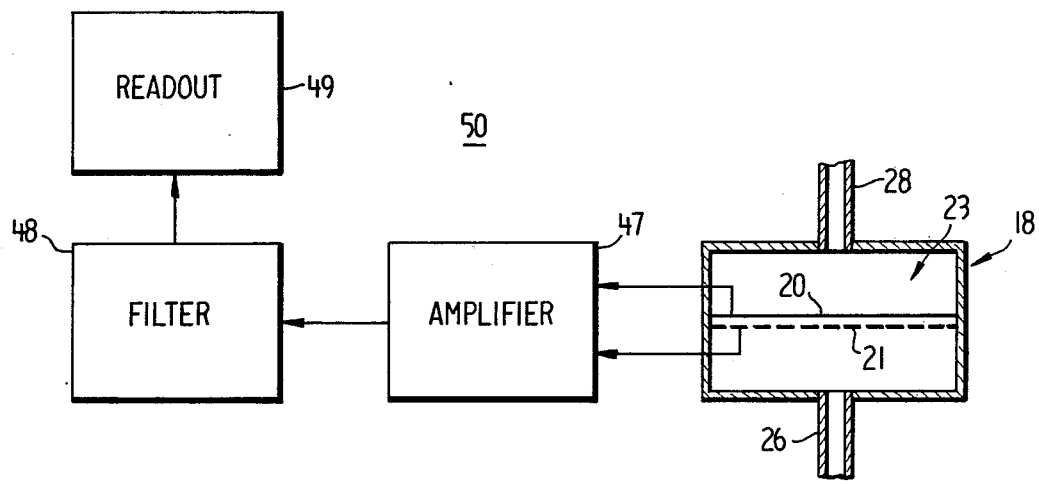
FIG. 3 is a schematic view of the transducing system used for converting pressure fluctuations occurring within the gas detecting transducer into electronic readout signals.

FIG. 3 illustrates the transducing system 50 used for converting the pressure variations occurring within the gas detecting transducer 10 illustrated in FIG. 1 into electronic readout signals. Diaphragm 20 is entirely electrically-conductive or has an electrically-conductive coating on the lower surface. An electrically-conductive grid 21 is adjacent to diaphragm 20 and electrically insulated from it. The diaphragm 20, grid 21, and the gas therebetween form a variable capacitor 23. As diaphragm 20 is displaced, the changes in capacitance of capacitor 23 are of the gas in chamber 12 and with an amplitude determined by the concentration of that same gas in sensed amplified in amplifier 47. The output of amplifier 47 is coupled to filter 48 which is a bandpass filter having a center frequency identical to the resonant frequency of the diaphragm 20. Filter 48 may be, for example, a phase locked loop such as LM 565 manufactured by National Semiconductor Corporation. The signal emanating from filter 48 is representative of the capacitance of capacitor 23, the displacement of diaphragm 20, and the amount of unknown gas in sample chamber 34. The output of filter 48 is coupled to readout 49. Readout 49 may be a device to indicate or record the filter output signal. Alternatively, readout 49 may be an alarm that is triggered in response to a predetermined gas level.

There is an alternate way to process the output of variable capacitor 23. A synchronous detector (not shown) may be substituted for filter 48. The second input of the detector is fed with a signal having the same frequency and phase as the chopper 32, and the output of the detector is connected to a read-out device.

Figure 2:
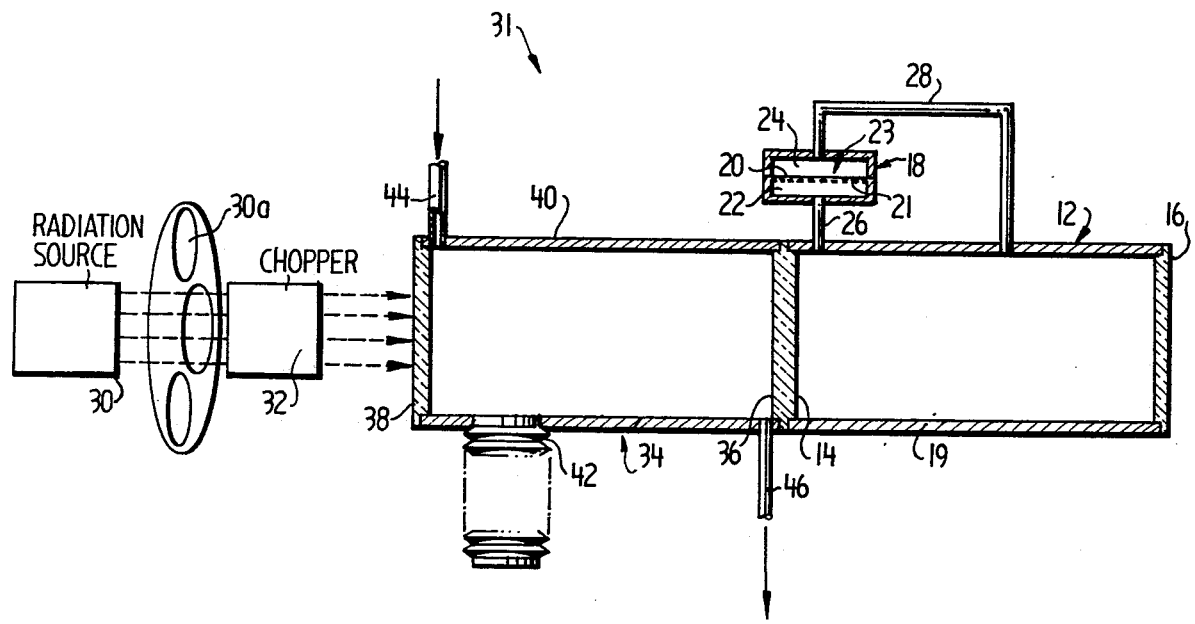
FIG. 2 shows the gas detecting transducer of the present invention used in conjunction with a spectroscopic gas analyzing system.
Figure 4:
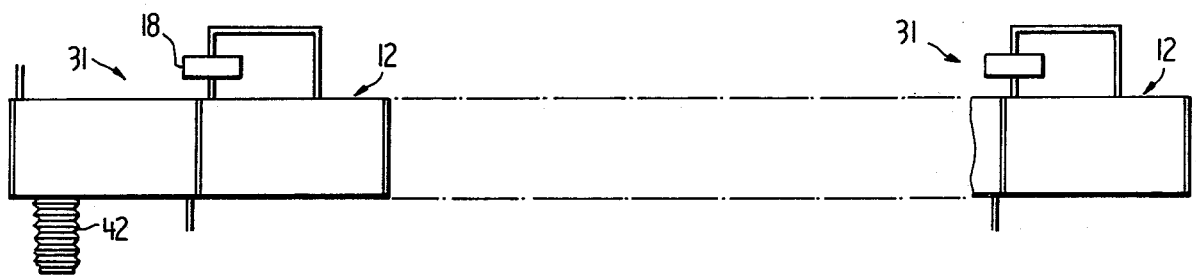
FIG. 4 is a view illustrating the serial connection of a plurality of the individual gas detecting transducers illustrated in FIG. 2.

The transducing system 50 illustrated in FIG. 3 also is used for transducing pressure fluctuations occurring within the apparatus illustrated in FIGS. 2 and 4.

Referring to FIG. 2, there is shown a spectroscopic system 31 incorporating a gas detecting transducer identical to the one shown schematically in FIG. 1. In FIG. 2, like numerals are used to identify like parts enumerated In FIG. 1. A sample chamber 34 containing an unknown gas is mounted to an end to end relation with the first chamber 12. Specifically, sample chamber 34 is closed by ends 36 and 38. Ends 36 and 38 are optically transparent to the range of wavelengths produced by radiation source 30 and passed by ends 14 and 16 of the first chamber 12. Inlet and exit ports, respectively 44 and 46, permit the changing of the gas sample contained within sample chamber 34 between successive tests. The cylindrical side wall 40 is highly reflective in a spectrum which contains the wavelengths that are absorbed by the gases contained within chamber 12 and 34. The cylindrical side wall 40 is provided with compressive means 42 which produce density variations within the sample chamber at the previously determined acoustical resonance frequency of chamber 12. Radiation passing directly through chamber 34 or passing therethrough as a result of reflection from the side wall 40 is reduced in intensity in the spectral regions characteristic of the gas of interest; the reduction in intensity being determined by the Beer-Lambert Law of Absorption and being subject to periodic variations as determined by that law and by the periodic density variations imposed on the gas within sample chamber 34 by compressive means 42. The radiation source 30 has the capability of sequentially introducing radiation of different spectrums which contain the specific wavelengths absorbed by the several separate gases. The radiation source 30 may comprise a source of radiation having a broad spectrum and a plurality of filters 30a each having a different narrower transmission spectrum that is contained within the broad spectrum. The filters are sequentially insertable within the radiation emitted by source 30. Other gases contained in chamber 34 will absorb selectively the region of their spectral activity and provide a spectrally localized modulation signature specific to each of the respective concentrations. Since the only absorbing gas in chamber 12 is the gas of interest, only that portion of the radiation passing through chamber 34 and modulated by the gas of interest will be subsequently further reduced by absorption in the chamber 12; that radiation being absorbed in gas portions proximate to window 14 while radiation in other regions of the spectrum passes therethrough without absorption. The intensity of the absorbed radiation is periodically varied at a frequency equal to the acoustical resonance frequency of the gas in chamber 12 and with an amplitude determined by the concentration of that same gas in chamber 34. The amplitude of the periodic pressure fluctuations in chamber 12 and the amplitude of the diaphragm vibrations, occurring at the acoustic resonant frequency, are representative of the concentration of the sought after gas in chamber 34.

While the system in FIG. 2 has been described as utilizing a single detecting transducer, it is nevertheless within the scope of the invention to use several gas detecting transducers in series as depicted in FIG. 4. A different sensitizing gas is employed in each transducer so that a plurality of gases may be detected simultaneously in the sample chamber. Of course the number of gases that can be detected simultaneously is directly dependent on the number of serially-connected chambers 12.

What is claimed is:

1. Gas detection apparatus comprising:
    a. a first chamber having a quantity of gas $x$ therein, said chamber having an acoustic resonant frequency;
    b. a second chamber with a pressure responsive diaphgram dividing said chamber into first and second parts, said diaphragm having a mechanical resonant frequency approximately equal to the acoustic resonant frequency of said first chamber;
    c. first coupling means for coupling the gas in said first chamber to said first part of said second chamber; said first coupling means permitting said gas pressure variations in said first chamber having a frequency equal to said acoustic resonant frequency to be transmitted to said first part of said chamber and said diaphragm;
    d. second coupling means for coupling the gas in said first chamber to said second part of said second chamber, said second coupling means permitting only average and low frequency gas pressure variations in said first chamber to be transmitted to said second part of said second chamber and said diaphragm;
    e. a third chamber containing an unknown gas in which gas $x$ may be present;
    f. a source of electromagnetic radiation that is intensity modulated at a frequency equal to said acoustic resonant frequency, said radiation including at least one spectrum that corresponds to an absorption spectrum of gas $x$;
    g. said third chamber having opposed end sections that are at least transparent to said spectrum, and said first chamber having at least one wall section that is at least transparent to said spectrum;
    h. said third chamber being positioned between said radiation source and said first chamber and said chambers being oriented to enable said electromagnetic radiation to pass through said third chamber and into said first chamber; and
    i. means for measuring the amplitude of the excursions of said diaphragm, said amplitude being representative of the amount of gas $x$ in said third chamber.

2. Gas detection apparatus as recited in claim 1 further comprising:
    a. means for varying the density of said unknown gas contained in said third chamber.

3. Gas detection apparatus as recited in claim 2 wherein said means for varying the density of said unknown gas contained in said third chamber comprises:
    a. a bellows disposed in a wall of said third chamber.

4. Gas detection apparatus as recited in claim 1 wherein said third chamber further comprises:
    a. an inlet and exit port for permitting the intake and exhaust of said unknown gas contained in said third chamber.

5. Gas detection apparatus as recited in claim 1 wherein:
    a. said first chamber, said second part of said second chamber, and said second coupling means comprise in combination a double Helmholtz resonator.

6. Gas detection apparatus as recited in claim 1 wherein:
    a. said first and second chambers are filled with known concentrations of different gases with dissimilar electromagnetic absorption spectra.

7. Gas detection apparatus as recited in claim 6 further including filter means interposed between said radiation source and said third chamber for sequentially enabling different bands of electromagnetic radiation to reach said third and first chambers.

* * * * *